United States Patent [19]

Veney

[11] 4,255,452

[45] Mar. 10, 1981

[54] COSMETIC COMPOSITION

[76] Inventor: Ruby G. Veney, 4520 Pine St., Philadelphia, Pa. 19143

[21] Appl. No.: 21,551

[22] Filed: Mar. 19, 1979

[51] Int. Cl.$^3$ .............................................. A61K 7/48
[52] U.S. Cl. .................................... 424/359; 424/365
[58] Field of Search ........................ 424/358, 359, 365

[56] References Cited

U.S. PATENT DOCUMENTS

| 3,959,491 | 5/1976 | Young et al. ......................... 424/365 |
| 4,148,875 | 4/1979 | Barnett et al. ........................ 424/365 |

FOREIGN PATENT DOCUMENTS

| 743882 | 6/1970 | Belgium ..................................... 424/359 |
| 2353861 | 5/1974 | Fed. Rep. of Germany ............. 424/83 |
| 2607849 | 5/1977 | Fed. Rep. of Germany ........... 424/365 |
| 2630560 | 1/1978 | Fed. Rep. of Germany ........... 424/359 |
| 2723682 | 4/1978 | Fed. Rep. of Germany ............. 424/83 |
| 1559204 | 1/1969 | France ..................................... 424/195 |
| 2213051 | 2/1974 | France ....................................... 424/80 |
| 2290889 | 6/1976 | France ....................................... 424/83 |

OTHER PUBLICATIONS

Amer. Perf. & Cosmetics, 1966, vol. 81, No. 12, pp. 43 to 51, (pp. 43, 44, 45, 46-49).
Martindale, Extra Pharmacopocia, 26th Edition, vol. I, pp. 667, 668 and 1287.

*Primary Examiner*—Dale R. Ore
*Attorney, Agent, or Firm*—Jacob Trachtman

[57] ABSTRACT

A cosmetic cream preparation for cleansing, soothing and moisturizing the skin basically comprising a mixture of non-fat dry milk solids, witch hazel and olive oil to which petroleum jelly, pantothenic acid, magnesium and water are added. An emollient and preservative may be added and if desirable a fragrance material may also be included. To cleanse the skin, the composition is applied and massaged gently, and may be applied before or after bathing to provide a refreshing and soothing effect.

1 Claim, No Drawings

COSMETIC COMPOSITION

The present invention relates to a cosmetic composition and method of making same, and particularly to a cream preparation for cleansing, smoothing and moisturizing the skin.

An object of the invention is to provide a new and improved composition for cleansing, smoothing and moisturizing the skin.

Another object of the invention is to provide a new and improved method for making a cosmetic preparation which is inexpensive and readily accomplished.

The cosmetic composition according to the present invention contains as the major components a mixture of water, non-fat dry milk solids, witch hazel, and olive oil, with the addition of petroleum jelly, pantothenic acid, and magnesium. An emollient such as polyoxyethglene and a preservative such as methytparaben may be added, and if desired a fragrance material may also be included.

More particularly the composition may contain 25 to 35 parts by weight of non-fat dry milk solids, 15 to 25 parts by weight of witch hazel, 35 to 45 parts by weight of olive oil and 150 to 200 parts by weight of water. In the preferred form, the composition also includes 0.5 to 2.2 parts by weight of petroleum jelly, 8 to 12 parts by weight of methylparaben, 1 to 2 parts by weight of polyoxyethylene, 0.005 to 0.02 parts by weight of pantothenic acid, and 0.005 to 0.02 parts by weight of magnesium. If desired 0.005 to 0.02 parts by weight of a fragrance material may be included.

The composition is prepared by thoroughly mixing by agitation at room temperature the witch hazel, non-fat dry milk solids, pantothenic acid and magnesium. Methyparaben and polyoxyethylene are each separately mixed with water and also added to the mixture. The olive oil is then slowly mixed into the mixture by gently agitation at room temperature. A fragrance material may also be added at this time. The resulting mixture solidifies to a cream texture and consistancy at room temperature.

As an example, a composition in accordance with the invention was made by the method of the invention utilizing about, 150 to 200 parts by weight water, 30 parts by weight non-fat dry milk solids, 20 parts by weight witch hazel, 40 parts by weight olive oil, 9.5 parts by weight methylparaben, 1.5 parts by weight polyoxythylene, 0.01 parts by weight pantothenic acid, 0.01 parts by weight magnesium, and 0.01 parts by weight fragrance. The composition was used by applying it to the skin and massaging gently. The composition may be used before or after bathing to provide a freshing and soothing effect. The composition may be applied to the entire body for leaving the skin soft, smooth and relaxed.

While certain proportions of the ingredients have been disclosed for preferred formulations, it should be understood that it is not intended that the scope of the invention be limited thereto, since it will be readily evident to those skilled in the art that various modifications can be made in the composition and method without substantially departing from the spirit of the invention.

What is claimed is:

1. A composition for cleansing, smoothing and moisturizing the skin consisting of a mixture of about 25 to 35 parts by weight non-fat dry milk solids, about 15 to 25 parts by weight witch hazel, about 35 to 45 parts by weight olive oil, and about 150 to 200 parts by weight of water.

* * * * *